United States Patent [19]

Branner-Jorgensen

[11] 4,386,160

[45] * May 31, 1983

[54] THERMAL DESTABILIZATION OF BACILLUS SERINE PROTEASES

[75] Inventor: Sven Branner-Jorgensen, Charlottenlund, Denmark

[73] Assignee: Novo Industri A/S, Denmark

[*] Notice: The portion of the term of this patent subsequent to Mar. 10, 1998, has been disclaimed.

[21] Appl. No.: 241,852

[22] Filed: Mar. 9, 1981

Related U.S. Application Data

[63] Continuation-in-part of Ser. No. 973,937, Dec. 28, 1978, Pat. No. 4,255,454.

[30] Foreign Application Priority Data

Jun. 23, 1980 [DK] Denmark .............................. 2674/80

[51] Int. Cl.³ .......................... C12N 9/54; C12N 9/96; C12N 9/50; C12N 9/56
[52] U.S. Cl. .................................... 435/221; 435/188; 435/219; 435/222
[58] Field of Search ............... 435/188, 219, 220, 221, 435/222, 223; 426/63

[56] References Cited

U.S. PATENT DOCUMENTS 3,723,250 3/1973 Aunstrup et al. ................... 435/221
3,886,042 5/1975 Blumberg et al. .............. 435/221 X
4,255,454 3/1981 Branner-Jorgensen ........ 435/223 X

FOREIGN PATENT DOCUMENTS 2045772 11/1980 United Kingdom .................. 426/63

OTHER PUBLICATIONS

Vratsanos S. M., On the Mechanism of Enzyme Action, LXXI, Acylations of Trypsin in Organic Solvents, Archives of Biochemistry and Biophysics, vol. 90, 1960 (pp. 132–138).

Primary Examiner—David M. Naff
Attorney, Agent, or Firm—Fidelman, Wolffe & Waldron

[57] ABSTRACT

Bacillus serine proteases are acylated with an acyl radical of a monocarboxylic or dicarboxylic acid of about 1 to 6 carbon atoms to thermally destabilize the proteases at least about 3° C. The acylated proteases have at least about 50% of their activity before acylation, and are advantageous in processes where it is desired to inactivate the proteases at a certain point in the process.

10 Claims, No Drawings

THERMAL DESTABILIZATION OF BACILLUS SERINE PROTEASES

RELATED APPLICATIONS

This application is a continuation-in-part of copending application Ser. No. 973,937, filed Dec. 28, 1978, for *A METHOD FOR THERMAL DESTABILIZATION OF MICROBIAL RENNET*, now U.S. Pat. No. 4,255,454.

The present invention relates to proteolytic enzymes and enzyme compositions and to methods of enzymatic protein hydrolysis. More particularly it relates to thermally destabilized Bacillus serine proteases and to methods of hydrolyzing proteins with such proteases including the thermal destabilization of the protease at a desired stage in the hydrolysis procedure.

BACKGROUND OF THE INVENTION

Proteases are widely used in a variety of contexts requiring the hydrolysis of proteins. It is possible to catagorize proteolytic hydrolysis processes into two general categories. One includes those procedures where the continuing presence of proteolytic activity after the accomplishment of the intended protein hydrolysis is of no concern. That category is conveniently typified by laundering operations with detergent formulations which contain proteases and by hide de-hairing processes employing protease formulations. In either case, the continuing presence of proteolytic activity is not material to the process.

A second category, and the context of concern in the present invention are those procedures where it is important to terminate proteolytic activity at some stage of the procedure, when a desired degree of protein hydrolysis is attained and when continuing activity would be undesirable or unacceptable.

The second category is typified by three convenient and commercially significant examples:

One is the protein hydrolysis of vegatable proteins, e.g. soy proteins, in order to produce a protein hydrolyzate with improved functional properties. Examples of such processes and the improvements in properties are set forth in U.S. Pat. Nos. 4,100,024 and 4,100,151, which are representative.

A second process is the protein hydrolysis carried out on animal proteins, such as the haemolyzed red blood corpuscle fraction of blood to obtain certain desired characteristics and properties in the hydrolyzate. A representative example of such a procedure is set out in Belgian Pat. No. 873,932.

A third process within the second category is the procedure employed in beer making known as chill-proofing which is in substance an enzymatic protein hydrolysis. Chill-proofing of beer is exemplified in U.S. Pat. No. 3,366,483.

In each of these processes, and in others of a like character, if proteolytic activity is still present after the conclusion of the intended degree of protein hydrolysis, the hydrolytic action will continue to a detrimental or undesired extent and begin to produce detrimental or undesired results. It is thus important to be able to deactivate the enzyme at the desired stage of the hydrolysis.

It is the ability to reliably and controllably deactivate proteolytic enzymes at the desired point in procedures such as those set forth above which is the object of the present invention.

The most usual technique for deactivating proteases is a heat treatment. Such heat treatments are simple and reliable, but are often accompanied by an unintended and detrimental degradation or denaturation of some proteins or protein hydrolyzates, which may unacceptably alter the properties or characteristics of the product.

Chemical deactivations have been developed, but are often limited in usefulness by one or more undesirable side effects or consequences thereof. Such techniques may, like heat treatments, degrade or denature the reaction products. They may also introduce undesirable or unacceptable by-products, such as toxic substances, adverse or off-taste components, or the like. In some cases chemical deactivation techniques may be prohibitively expensive.

It is accordingly an object of the present invention to provide Bacillus serine proteases which have been modified in such fashion that the thermal stability thereof is reduced to a level at which the proteolytic activity may be deactivated by a heat treatment under conditions sufficiently gentle that it will not degrade or denature the protein or protein hydrolyzate of the reaction product.

BRIEF DESCRIPTION OF THE INVENTION

It has been found that Bacillus serine proteases may be made susceptible to thermal destabilization by acylation, preferably with $C_1$ to $C_6$ acylating agents, such as the active acylating forms of monocarboxylic or dicarboxylic acids, particularly anhydrides thereof, although the corresponding acyl halides and the like may also be employed.

More particularly, the present invention discloses a thermally de-stabilized Bacillus serine protease, acylated by an active acylating derivative of a monocarboxylic acid or dicarboxylic acid of about 1 to 6 carbon atoms where the degree of acylation is sufficient to produce a degree of destabilization of a least 3° C., preferably at least about 5° C., and most preferably about 5° to 15° C., all at a pH of 7.5, where the degree of destabilization is as hereinafter defined, and at a loss of proteolytic activity of less than about 50%, preferable less than about 25%, and still more preferably, loss than about 10%.

DETAILED DESCRIPTION

It has been found that the Bacillus serine proteases acylated according to the invention is significantly destabilized and that the degree of destabilization suffices to meet the requirements for protease utilization without having detrimental effect on storage stability of the enzyme preparation.

The destabilizing result is believed to be surprising, as it appears from Agric. Biol. Chem. 41 (11), 2163-2168 (1977) that acetylation of egg white causes a thermal stabilization.

Proteolytic activity in the instant application is measured in Anson units, as determined according to the modified Anson method described in *NOVO ENZYME INFORMATION BULLETIN* No. 058e-GB. The original Anson method is described in J. Gen. Physiol 22, 79-89 (1939).

Since this invention relates to a controlled thermal destabilization of Bacillus serine proteases, some elaboration is provided below on techniques to measure thermal stability and to quantify the reduction in thermal stability, the reduction being expressed in °C.

Under ideal conditions, an enzyme may be denatured at a suitable (high) temperature level in such a way that the residual activity of the enzyme decreases as a function of time along an exponential decay curve, i.e., with a well-defined half life, the half life being a function of the temperature (°C.). The half life $T_{\frac{1}{2}}$ can be calculated according to the formula $$T_{\frac{1}{2}} = \frac{(t_2 - t_1) \ln 2}{\ln A_1 - \ln A_2}$$

where $A_1$ is the enzyme activity measured after heating to a specified temperature for the time $t_1$, whereas $A_2$ is the enzyme activity measured after heating to the same specified temperature for the time $t_2$. The half life will be shorter at the higher temperature, everything else being equal. For many enzymes, a change in the pH of the enzyme solution and the ion strength, and the presence of certain salts will influence the half life substantially. Furthermore, chemical derivatization of the enzyme can change the half life considerably. If a chemical derivatization of a particular enzyme causes thermal destabilization of the enzyme, the degree of destabilization is said to be n°C., if the original (non-derivatized) enzyme and the derivatized enzyme have the same half life at N°C. and (N−n)°C. respectively.

In a more fundamental derivation, and one which may be more useful, the stability of the enzyme is evaluated by means of a heat treatment of the enzyme subsequent to dilution in 1/15 M phosphate buffer at pH 7.5. If the heat treatment is performed at two different temperatures $T_1$ and $T_2$ the thermodynamic parameters A and E can be calculated by means of the Arrhenius equations $$k_1 = A \cdot e^{-(E/RT_1)}$$

$$k_2 = A \cdot e^{-(E/RT_2)}$$

where R is the gas constant ($1.9865 \text{ cal} \times °C.^{-1} \times \text{mol}^{-1}$), T is the absolute temperature (°K.), A is the preexponential or frequency factor, E is the activation energy for the heat inactivation process (which may be expressed in cal/mol) and k is the velocity constant for the heat inactivation, whereby k under the supposition of a decay curve of the first order for the heat inactivation may be calculated by means of the formula $$k = (\ln a_o - \ln a_t)/t$$

in which $a_o$ and $a_t$ is the protease activity in Anson units referred to the same quantity before and after heat treatment during the time t (which may be expressed in minutes).

By solving the two above Arrhenius equations E and A may be calculated i.e. according to the equations $$E = \left(\frac{1}{T_1} - \frac{1}{T_2}\right)^{-1} R \ln \frac{k_2}{k_1}$$

$$A = k_1 \cdot e^{\frac{T_2}{T_2 - T_1} \ln \frac{k_2}{k_1}}$$

If the velocity constant k of the native enzyme is calculated for a temperature of 60° C. (the reference temperature $T_{Ref}$), and if the values of A and E for the modified enzyme is determined according to the above indicated equations, the temperature $T_D$, at which the modified enzyme is inactivated at the same rate with which the native enzyme is inactivated at the temperature $T_{ref}$, can be calculated by means of the equation $$T_D = \frac{E}{R(\ln A - \ln k)}$$

The destabilization of the modified enzyme is defined as $(T_{Ref} - T_D)°C$.

Unless otherwise stated, all destabilization values in this specification are measured at pH 7.5 since the results of the destabilization measurement are pH dependent.

Normally, the acylation method of this invention is accompanied by some activity loss attributable to product losses in the procedure, and it has been found that for economic reasons, the destabilization should not be carried further than an activity loss of around 50%. It will be preferred in most cases, and attainable with essentially all Bacillus serine proteases, to achieve an acceptable degree of destabilization, at least about 3° C., preferably at least about 5° C., and most preferably about 5° to 15° C., with an activity loss of less than 50%. It is still more preferred, for readily apparent reasons, to attain the necessary or desired degree of destabilization at an activity loss of less than about 25%, and even more preferred, at an activity loss of less than about 10%. In a few instances, an increase in activity has been observed.

It is worth mentioning that the acylation procedure in accordance with this present invention, while it results in an activity loss in most cases, does not alter the functional characteristics of the enzyme. It has been found, surprisingly, that the acylated Bacillus serine proteases exhibit hydrolysis kinetics which are identical with the properties of the unmodified enzyme.

As a general proposition, activity loss and degree of destabilization will vary with the selection of an acylating agent. The highest degree of destabilization for any given enzyme, i.e., around 15° C., will ordinarily be attained by the use of acetic anhydride. By the same token, acetic anhydride can also be expected to result in the greatest activity losses, of about 50% (or even more if acylation is continued, although such is generally not indicated).

Butyric acid acylation will most often result in substantially no change in activity, and, in corresponding fashion, rather modest degree of destabilization, i.e., about 3° to 5° C.

For any given protease, if there is to be any increase in activity, it will generally be observed by acylation with succinic or maleic anhydride. The degree of destabilization with these acylating agents may range over the entire spectrum of 3° to 15° C. for differing enzymes.

The base catalysed acylation of the enzymes proceeds in well known fashion with ease. The acylation reaction is described for subtilisin Carlsberg and subtilisin BPN' at Carlsberg Res. Commun., Vol. 41, No. 5, 1976, page 242 et seq. See also U.S. Pat. No. 3,886,042.

In most circumstances, acylation with monocarboxylic acid derivatives are consistent and predictable results are attained thereby. A given objective for a specific intended use can be obtained with reliability with these agents.

Bacillus serine proteases per se are widely known and as such are generally available from, inter alia, B. subtilis, B. licheniformis, B. pumilus, B. amyloliquificaciens, B. alcalophilus, and the Bacillus species described in U.S. Pat. No. 3,723,250.

A preferred embodiment of the method according to the invention comprises acylating with the anhydride of a monocarboxylic acid with between 1 and 6 carbon atoms.

Another preferred embodiment of the method according to the invention comprises destabilization of subtilisin Carlsberg.

Another preferred embodiment of the method according to the invention comprises the use of an active derivative of acetic acid as the acylating agent, preferably acetic anhydride.

Another preferred embodiment of the method according to the invention comprises the use of propionic anhydride as the acylating agent.

Another preferred embodiment of the method according to the invention comprises acylating with a weight proportion in the reaction mixture between the acylating agent and the total amount of protein in the enzyme preparation of between 0.1 and 1.

There is a degree of acylation at which the degree of destabilization is maximized for each combination of enzyme and acylating agent. A greater degree of acylation is generally not desirable, as there will ordinarily to be a greater and greater activity loss and no off-setting benefit to be obtained. Thus it will generally be preferred to acylate to the extent appropriate to attain the maximum degree of destabilization and not more. The maximum is conveniently ascertained for a given combination of enzyme and acylating agent by reiteration.

The invention is now described in still more detail in reference to the following specific examples:

EXAMPLE 1

10 g of a subtilisin Carlsberg concentrate, sold under the trade mark ALCALASE ®, With proteolytic activity of 10.3 Anson units/g was suspended in 250 ml 0.1 M phosphate buffer with pH 9.5. To the suspension was added a solution of 2.5 g maleic anhydride in 12.5 ml tetrahydrofuran dropwise during 50 minutes. pH was kept constant at 9.5 during the dropwise addition by means of a pH stat with 4 N NaOH. The base consumption was 11.3 ml. The maleylated protease was now precipitated by addition of 140 g of $(NH_4)_2 SO_4$, and simultaneously the pH was adjusted to 7.5. The precipitated, maleylated protease was filtrated off with 5 g of diatomaceous earth and dried. The yield of dried product was 16.4 g with an activity of 7.8 Anson units/g. Thus, the activity yield was around 125%.

For determination of activity and thermostability solutions of untreated and maleylated protease were prepared, whereby these solutions contained about 0.2 Anson units/l in 1/15 molar phosphate buffer at pH 7.5. The thus diluted samples of maleylated protease were heat treated at 45° and 50° C. respectively for 30 minutes, whereas the sample of untreated protease was heat treated at 60° C. and the residual activity in the heat treated solutions were determined, vide the table 1 below.

TABLE 1

| protease | heat treatment temperature, °C. | residual activity after 30 minutes, % | destabilization, °C. (reference tem. 60° C.) |
|---|---|---|---|
| maleylated ALCALASE ® | 45 | 49.6 | 18 |
|  | 50 | 4.2 |  |
| untreated ALCALASE ® | 60 | 74.8 | 0 |

EXAMPLE 2

A concentrate of subtilisin Carlsberg, sold under the trade mark ALCALASE ®, with an activity of 9.4 Anson units/g was used for preparation of 4% suspension in 1.0 M phosphate buffer with a pH value of 9. The pH of the suspension was around 7.5.

To three 50 ml portions of this suspension was added 0.25, 0.5 and 1 g maleic acid anhydride, respectively, dissolved in 1 ml tetrahydrofuran. This addition was carried out during 1 hour at pH stat control (pH 8.5) with 4 N NaOH.

Similarly, to three other 50 ml portions of this suspension was added 0.25, 0.5 and 1 g solid succinic acid anhydride, respectively.

The thus prepared protease derivatives together with an untreated reference portion were diluted with 1/15 molar phosphate buffer at pH 7.5. Then the diluted protease derivatives were heat treated at 50° and 55° C., whereas the diluted reference was heat treated at 60° C. Subsequent to activity determinations the activity yield, the residual activity after heat treatment and destabilization in °C. were calculated. See Table 2.

TABLE 2

| protease | dosage of acylating agent g/g ALCALASE ® | activity yield, % | treatment temperature, °C. | time, min. | residual activity, % | destabilization, °C. (reference temperature 60° C.) |
|---|---|---|---|---|---|---|
| maleyated ALCALASE | 0.125 | 134 | 50 | 30 | 23.8 | 14 |
|  |  |  | 55 | 10 | 2.5 |  |
|  | 0.25 | 137 | 50 | 30 | 6.8 | 17 |
|  |  |  | 55 | 10 | 0.9 |  |
|  |  |  | 50 | 30 | 15.6 |  |
|  | 0.50 | 114 | 55 | 10 | 0.6 | 15 |
| succinylated ALCALASE | 0.125 | 107 | 50 | 30 | 85.4 | 4 |
|  |  |  | 55 | 30 | 68.1 |  |
|  | 0.250 | 109 | 50 | 30 | 78.9 | 7 |
|  |  |  | 55 | 30 | 54.6 |  |
|  |  |  | 50 | 30 | 47.8 |  |
|  | 0.500 | 122 | 55 | 30 | 15.2 | 13 |
| untreated ALCALASE ® | — | 100 | 60 | 30 | 64.2 | 0 |

EXAMPLE 3

1 g of a subtilisin Carlsberg concentrate, sold under the trade mark ALCALASE ®, with an activity of 10.1

Anson units/g was suspended in 10 ml ion exchanged water and filtered. The filter was rinsed with a saturated solution of sodium acetate, and the volume of the filtrate was adjusted to 25 ml with a saturated solution of sodium acetate.

To 20 ml of this solution at about 5° C. was added 4×50 μl acetic anhydride during approximately 1 hour. The pH value was adjusted to 8-9 by means of solid potassium carbonate during the reaction. Then the reaction mixture was transferred to a 50 ml measuring flask, and the volume was adjusted to 50 ml by means of ion exchanged water.

Samples of acetylated protease and of the reference solution was diluted with 1/15 molar phosphate buffer (pH 7.5). The activity was determined before and after heat treatment, as specified in the following table, from which also activity yield and destabilization appear. See Table 3.

TABLE 3

| protease | activity yield, % | heat treatment temperature, °C. | time, minutes | residual activity after heat treatment, % | destabilization, °C. (reference temperature 60° C.) |
| --- | --- | --- | --- | --- | --- |
| acetylated ALCALASE® | 71.2 | 45 | 30 | 49.2 | 17 |
| | | 50 | 30 | 14.4 | |
| untreated ALCALASE® | 100 | 60 | 30 | 60.3 | 0 |

EXAMPLE 4

3 g of Bacillus pumilus protease with an activity of 1.3 Anson units/g was suspended in 75 ml of 0.1 M phosphate buffer with pH 9,0. Hereby the pH value dropped to 5.9. With pH-stat control at 8.5 with addition of 4 N sodium hydroxide 0.98 g of maleic acid anhydride, dissolved in 2 ml tetrahydrofuran, was added. The addition was carried out during 45 minutes. The mixture was left for 15 minutes and then the pH value was adjusted to 7.5. Subsequently the reaction mixture was transferred to a 100 ml measuring flask, which was filled up to the mark with 1/15 M phosphate buffer of pH 7.5. Then this sample and a corresponding reference sample, which was not treated with maleic acid anhydride, was diluted to about 0.2 Anson units/l and heat treated. Reaction conditions and results appear from the following table 4.

TABLE 4

| enzyme | Activity yield, % | heat treatment temp. °C. | time, min. | Residual activity, % | Destabilization, °C. |
| --- | --- | --- | --- | --- | --- |
| Maleyated Bac. pumilus protease | 41.9 | 45 | 10 | 34.4 | 11 |
| | | 50 | 10 | 4.0 | |
| Untreated Bac. pumilus protease | — | 60 | 10 | 8.1 | — |

EXAMPLE 5

In a way corresponding to example 4.3 g of an enzyme concentrate with an activity of 8.0 Anson units/g and produced by means of the microorganism NCIB 10309 according to U.S. Pat. No. 3,723,250 was maleylated.

The reaction conditions and results appeal from the following table 5.

TABLE 5

| enzyme | Activity yield, % | Heat Treatment Temp. °C. | time, min. | Residual activity % | Destabilization °C. |
| --- | --- | --- | --- | --- | --- |
| Maleyated enzyme | 31.3 | 50 | 30 | 70.8 | 5.2 |
| | | 60 | 10 | 8.0 | |
| Untreated enzyme | — | 60 | 30 | 21.3 | — |

EXAMPLE 6

In a way corresponding to Example 4.3 g of a subtilisin Carlsberg concentrate, sold under the trade mark ALCALASE®, with an activity of 10.6 Anson units/g was citraconylated with 1.12 g citraconic anhydride dissolved in 2 ml of tetrahydrofuran. The reaction conditions and results appear from the following table 6.

TABLE 6

| enzyme | Activity yield, % | Heat Treatment temp. °C. | time, min. | Residual activity % | Destabilization, °C. |
| --- | --- | --- | --- | --- | --- |
| Citraconylated ALCALASE® | 79.2 | 45 | 30 | 20.5 | 20 |
| | | 50 | 10 | 23.6 | |
| Untreated ALCALASE® | — | 60 | 30 | 56.5 | — |

EXAMPLE 7

A. Isoelectric soluble soy protein hydrolyzate was produced in the laboratory according to the principles described in U.S. Pat. No. 4,100,024, Examples 1 and 2, and the experimental details were as follows:

800 ml of a suspension containing 8.0% (N×6.25) of soy protein isolate (Purina 500 E) was hydrolysed with a subtilism Carlsberg preparation, sold under the trade mark ALCALASE® 0.6 L at pH 8.0, using the pH-stat technique. The enzyme dosage was 20 AU/kg substrate, and the temperature was 40° C. Base consumption was recorded during the hydrolysis and used for plotting the hydrolysis curve, as described in Adler-Nissen and Sejr Olsen, ACS Symposium Series, No. 92, p. 125-146, Functionality and Protein Structure, 1979 (for the sake of brevity in the following referred to as Ref. I). When a DH value of 10% was reached, malic acid was added to pH 4.0. After 30 minutes at 50° C. and pH 4.0 (to ensure complete inactivation of the enzyme) the suspension was centrifuged at 3000×g for 15 minutes and the supernatant was filtered and carbon treated at pH 5.0 (pH adjustment with NaOH), as described in U.S. Pat. No. 4,100,024. The finished hydrolyzate was evaluated organoleptically by experienced persons under two different sets of conditions:

(a) 4% (N×6.25) and pH 6.5

(b) 3% (N×6.25), pH 4.5 and 8% sucrose.

The first set of conditions has been found to be optimal with respect to evaluating bitterness (Ref. I), whereby the second set of conditions simulate a protein enriched soft drink and are optimal for evaluating the general quality of the hydrolyzate.

B. A hydrolysis was carried out as in part A of this example except that the destabiized subtilisin Carlsberg from Example 3 was used instead of Alcalase 0.6 L in a dosage of 15 AU/kg of substrate.

By means of the organoleptic evaluations described in part A of this example, the hydrolyzate produced in this part B of this example was found to be indistinguishable from the hydrolyzate in part A of this example. Both hydrolyzates were found to be as desired, i.e. bland, non-bitter and clear. Also with respect to protein yield (68% solubilized protein in part A of this example and 67% solubilized protein in part B of this example) and malic acid consumption (18.6 g versus 18.8 g), the two hydrolyzates must be considered identical.

C. A hydrolysis was carried out as described in part B of this example, except that the enzyme dosage was 45 AU/kg of substrate.

The hydrolysis curve prepared in accord with FIG. 1 of Ref I, at 131, can be compared with the hydrolysis curve from example 7A. For any given value of the ordinate DH, these curves are found to be coincident within the limits of reproducability of the technique as reported in Ref. I. Enzymatic hydrolysis of soy protein for nutritional fortification of low pH food, Paulsen and Anderson, Ann. Nutr. Alim., 1978, Vol. 32, pages 205–216, (for the sake of brevity in the following referred to as Ref. II), the ratio of the hydrolysis times (t) for the two curves can be calculated by the formula $$(DH = (h/h_{tot}) \times 100\%, \text{ where } h_{tot} = 7.75 \text{ meqv./g})$$

and it is found that this ratio is constant (i.e., the variations is statistically non significant, when compared with repetitions of hydrolyses under identical conditions). This means that the reaction rate for any h-value relative to the initial reaction rate is the same for the two experiments and this implies identity with respect to the hydrolysis kinetics, cf. the discussions in Ref. II. In comparison two different proteases will often exhibit significantly different hydrolysis curves as exemplified by FIG. 1 in Ref. I.

I claim:

1. A method for reducing the thermal stability of Bacillus serine protease by acylation, comprising acylating said protease with an acyl radical of a monocarboxylic or dicarboxylic acid of about 1 to 6 carbon atoms to a reduced thermal stability of at least about 3° C. and having at least about 50% of the proteolytic activity before acylating.

2. The method of claim 1 wherein said reduced thermal stability is from about 3° C. to about 15° C.

3. The method of claim 1 wherein said reduced thermal stability is from about 5° C. to about 15° C.

4. The method of claim 1 wherein said activity is at least about 70% of the proteolytic before acylating.

5. The method of claim 1 wherein said activity is at least about 90% of the proteolytic activity before acylating.

6. The method of claim 1 wherein said acid is a monocarboxylic acid selected from the group consisting of acetic, propionic, butyric.

7. The method of claim 1 wherein said acid is a dicarboxylic acid selected from the group consisting of maleic and succinic acids and mixtures thereof.

8. The method claim 1 wherein said protease is subtilisin Carlsberg.

9. A thermally destabilized Bacillus serine protease acylated with an acylating derivative of a monocarboxylic acid containing about 1 to 6 carbon atoms to a reduced thermal stability of at least about 3° C. at pH 7.5 and having at least about 50% of the proteolytic activity before acylating.

10. The protease of claim 9 wherein said protease is subtilisin Carlsberg.

* * * * *